(12) United States Patent
Boden et al.

(10) Patent No.: US 6,468,949 B2
(45) Date of Patent: Oct. 22, 2002

(54) CYCLOHEXENYL CYCLOPROPYL KETONE

(75) Inventors: Richard M. Boden, Ocean, NJ (US); William L. Schreiber, Freehold, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 10/013,290

(22) Filed: Dec. 10, 2001

(65) Prior Publication Data

US 2002/0107154 A1 Aug. 8, 2002

Related U.S. Application Data

(63) Continuation-in-part of application No. 09/734,850, filed on Dec. 12, 2000, now abandoned.

(51) Int. Cl.[7] .............................. C11D 3/20; A61K 7/46; C07C 45/61; C07C 49/533; C07C 49/543
(52) U.S. Cl. ...................... 510/106; 512/24; 568/329; 568/343
(58) Field of Search ...................... 512/24; 510/106; 568/309, 329

(56) References Cited

U.S. PATENT DOCUMENTS

| | | | |
|---|---|---|---|
| 4,198,309 A | 4/1980 | Mookherjee et al. |
| 4,292,447 A | 9/1981 | Trenkle et al. |
| 4,460,792 A | 7/1984 | Schulte-Elte et al. |
| 4,534,891 A | 8/1985 | Boden et al. |
| 6,025,527 A | 2/2000 | Boden et al. |
| 6,051,548 A | 4/2000 | Boden et al. |

FOREIGN PATENT DOCUMENTS

EP    0 009 540    4/1980

*Primary Examiner*—John Hardee
(74) *Attorney, Agent, or Firm*—Joseph F. Leightner

(57) ABSTRACT

The present invention is directed to cyclopropyl-2,6,6-trimethylcyclohex-3-enyl ketone and is use in creating perfumes and scents in such items as perfumes, colognes, toilet water and personal care products.

13 Claims, No Drawings

CYCLOHEXENYL CYCLOPROPYL KETONE

This is a Continuation-in-Part (CIP) of prior application Ser. No. 09/734,850, filed Dec. 12, 2000, now abandoned.

FIELD OF THE INVENTION

The present invention relates to new chemical entities and the incorporation and use of the new chemical entities as fragrance chemicals.

BACKGROUND OF THE INVENTION

There is an ongoing need in the fragrance industry to provide new chemicals to give perfumers and other persons ability to create new fragrances for perfumes, colognes and personal care products.

In our previous work, described in U.S. Pat. Nos. 6,025,527 and 6,051,548, hereby incorporated by reference as if set forth in their entirety, cyclohexenyl cyclopropyl ketone analogs are described.

While these materials are useful in producing compounds that are suitable for use as fragrance ingredients; the reaction is limited in the ketone products that are possible. As is well appreciated by those in the fragrance industry, chemical analogs and homologs, as well as small changes in the chemical structure of a molecule, can impart significant and different fragrance characteristics to the molecule. In view of this, there is an ongoing need to be able to produce other related compounds to determine if these compounds have unique properties and if these compounds are suitable for incorporation in fragrance formulations.

SUMMARY OF THE INVENTION

The present invention provides a novel compound, incorporation of the compound to provide a fragrance to perfumes, toilet water, colognes, personal products and the like. In addition, the present invention is directed to the use of related compounds as a fragrance in perfumes, toilet water, colognes, personal products and the like.

More specifically, the present invention is directed to cyclopropyl-2,6,6-trimethylcyclohex-3-enyl ketone, which is set forth below.

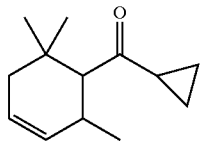

In another embodiment of the invention is a method for enhancing, modifying or augmenting a product by incorporating an olfactory acceptable amount of the compound into a fragrance formulation. A method for making the claimed compound is also described.

These and other embodiments of the present invention will be apparent by reading the following specification.

DETAILED DESCRIPTION OF THE INVENTION

The present invention is directed to the compound cyclopropyl-2,6,6-trimethylcyclohex-3-enyl ketone and the use of the compound in fragrance.

The compound is prepared by a two-step reaction sequence that is preferably conducted in a single pot. Generically, the reaction is described as the reaction of 4-acetyl-3,5,5-trimethylcyciohexene with a $(C_1-C_6)$alkyl magnesium chloride, preferably, butyl magnesium chloride and bromochloroethanie.

The reaction as set forth below provides the chlorinated adduct:

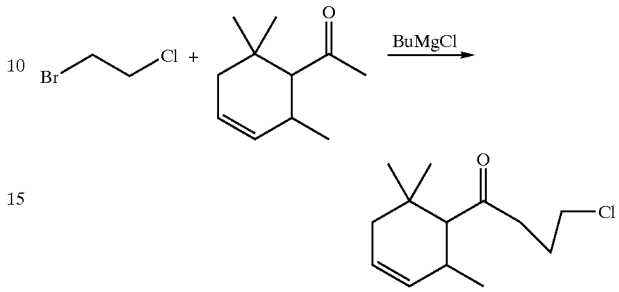

followed by the formation of the cyclopropyl ring, which is created by the heating of the chlorinated adduct:

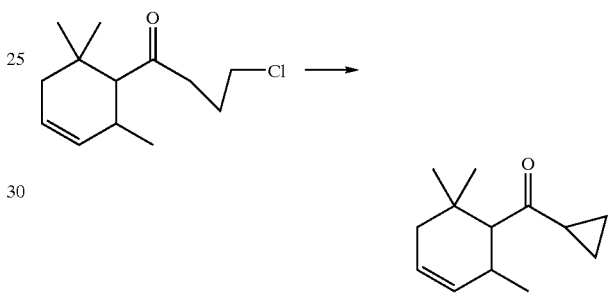

The odor characteristic of the compound is described as more floral, less minty and less fruity than the analog compounds set forth in U.S. Pat. Nos. 6,025,527 and 6,051,548. The cyclopropyl-2,6,6-trimethylcyclohex-3-enyl ketone compound was also found to possess a desirable cooling characteristic that the other cyclohexenyl cyclopropyl compounds in U.S. Pat. Nos. 6,025,527 and 6,051,548 did not possess.

The use of this compound is widely applicable in current perfumery products including the preparation of perfumes and colognes, the perfuming of personal care products, such as soaps, shower gels and hair care products As well as air fresheners and cosmetic preparations. The present invention can also be used to perfume cleaning agents, such as, but not limited to, detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can be additionally used in the various preparations are known to those with skill in the art.

Many types of fragrances can be employed in the present invention, the only limitation being the compatibility with the other components being employed. Suitable fragrances include, but are not limited to, fruits such as almond, apple, cherry, grape, pear, pineapple, orange, strawberry, raspberry; musk; flower scents such as lavender-like, rose-like, iris-like and carnation-like. Other pleasant scents include herbal scents, such as rosemary, thyme, basil and lavender, and woodland scents derived-from pine, spruce and other forest smells. Fragrances may also be derived from various oils, such as essential oils, or from plant materials, such as peppermint, spearmint and the like.

A list of suitable fragrances is provided in U.S. Pat. No. 4,534,891, the contents of which are incorporated by reference as if set forth in their entirety. Another source of suitable fragrances is found in *Perfumes Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea,. trefle, tuberose,- vanilla, violet, wallflower and the like.

Olfactory effective amount is understood to mean the amount of compound in perfume compositions the individual component will contribute its particular olfactory characteristics, but the olfactory effect of the perfume composition will be the sum of the effects of each of the perfume or fragrance ingredients. Thus, the compound of the invention can be used to-alter the aroma characteristics of the perfume composition, or by modifying the olfactory reaction contributed by another ingredient in the composition. The amount will vary depending on many. factors, including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the fragrance, other agents can be used, such as surfactants, emulsifiers and polymers to encapsulate the fragrance, without departing from the scope of the present invention.

Another method of reporting the level of the compound of the invention in the perfumed composition, i.e., the compound as a weight percentage of the materials, is added to impart the desired fragrance. The compound of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compound of the invention to provide the desired fragrance and intensity.

Another advantage of the present compound is that its fragrance has been found to be complimentary to δ-damascone, α-damascone and β-damascone. This allows the cyclopropyl-2,6,6-trimethylcyclohex-3-enyl ketone to be used in combination with these commercially available fragrance materials. In another embodiment of the invention, a fragrance mixture is provided that contains multiple compounds including (a) first compound cyclopropyl-2,6,6-trimethylcyclohex-3-enyl ketone and (b) at least one compound selected from the group: α-damascone, β-damascone and γ-damascone; wherein the weight of the first compound cyclopropyl-2,6,6-trimethylcyclohex-3-enyl ketone provided in said fragrance mixture is greater than the weight of the second material selected from the group consisting of δ-damascone, β-damascone, α-damascone and mixtures of δ-damascone, β-damascone and α-damascone. Preferably, the weight ratio of cyclopropyl-2,6,6-trimethylcyclohex-3-enyl ketone to the damascone materials, either alone or in mixtures with one another, is generally from about 1.5:1 to about 10: 1, preferably from 2:1 to about 8:1, most preferably from about 3:1 to about 5:1.

The following examples are provided as specific embodiments of the present invention. Other modifications of this invention will be readily apparent to those skilled in the art. As used herein, all percentages are weight percent.

EXAMPLE 1

Preparation of Cyclopropyl 2,6,6-Trimethylcyclohex-3-Enyl Ketone

Butyl magnesium chloride provided in ether (1050 milliliters) was charged to a reaction vessel equipped with a stirrer, heating unit and equipment suitable for conducting vacuum distillation. 4-acetyl-3,3,5-trimethylcyclohexene, which is described and prepared in the literature, see K. S. Ayyar, R. C. Cookston, and A. Kagi, *Journal Chemical Society Perkin*, 1725 (1975); step 1 (250 grams) was added at room temperature, with the constant release of butane gas. Bromochloroethane (228 grams) was added at 25° C. over one hour. 250 Milliliters of 1-methyl-2-pyrrolidinone was then added to the reaction mixture, and the temperature of there action mixture was increased to about 42° C. for about one hour. The temperature was then raised to 60° C. while distilling off ether. The pot temperature was raised to 70° C. and maintained at that temperature for about 24 hours. Aqueous acetic acid (200 grams, 10 weight percent) was then added to the reaction mass. The aqueous layer was separated and discarded. The organic layer was washed a single time with 500 milliliters of 10% salt solution. Distillation provided approximately 249 grams of product. (boiling point 126° C. at 3 millimeters) The 1H data was recorded on a BRUKER DMX Advance 360 MHz NMR with TMS as a reference:

0.71–0.81 (m, 2H), 0.85–0.91 (ms, 6H), 0.91–0.97 (m, 1H), 1.01–1.09 (m, s, 4H), 165–1.75 (m, 1H), 1.85–1.93 (m, 1H), 1.95–2.04 (m, 1H), 2.36–2.41(m, 1H), 2.46–2.57 (m, H), 5.40–5.52 (m, 2H).

EXAMPLE 2

The following mixture was prepared:

| Ingredients | Parts by Weight |
| --- | --- |
| Rhodinol | 270.0 |
| Nerol | 90.0 |
| Linalool | 30.0 |
| Terpineol | 30.0 |
| Phenylethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenylethyl acetate | 20.0 |
| Rose oxide | 8.0 |
| Guaiacol | 30.0 |
| l-Citronellal | 90.0 |
| Neryl acetate | 3.0 |
| Clove bud oil | 1.0 |
| Cadinene | 2.0 |
| Guaiene | 1.0 |
| Gum turpentine | 12.0 |
| α-Pinene | 1.0 |
| Myrcene | 5.0 |
| Limonene | 2.0 |
| p-Cymene | 1.0 |

To the foregoing mixture 30 parts by weight of cyclopropyl-2,6,6-trimethylcyclohex-3-enyl ketone was added. The above fragrance was described as having a more floral character than the comparative formulation found in U.S. Pat. No. 6,025,527, Example II, in which the isomer was used.

What is claimed is:

1. The compound cyclopropyl-2,6,6-trimethylcyclohex-3-enyl ketone.

2. The compound of claim 1 incorporated in perfumes, colognes, toilet water and personal care products.

3. The compound of claim 2 wherein the personal care product is selected from the group consisting of detergents, dishwashing compositions, scrubbing compounds and window cleaners.

4. A method for performing a product by incorporating an olfactory acceptable amount of the compound of claim 1.

5. The method of claim 4 wherein the product is incorporated in perfumes, colognes, toilet water, cleaning products and personal care products.

6. The method of claim 5 wherein the cleaning product is selected from the group consisting of detergents, dishwashing compositions, scrubbing compounds and window cleaners.

7. A fragrance mixture which contains multiple compounds including (a) a first compound cyclopropyl-2,6,6-trimethylcyclohex-3-enyl ketone and (b) a second compound selected from the group: α-damascone, β-damascone and γ-damascone.

8. The fragrance mixture of claim 7 wherein the weight of the first compound cyclopropyl-2,6,6-trimethylcyclohex-3-enyl ketone provided in said fragrance mixture is greater than the weight of the second material selected from the group consisting of δ-damascone, β-damascone, α-damascone and mixtures of δ-damascone, β-damascone, α-damascone.

9. The fragrance mixture of claim 8 wherein the weight ratio of the first compound cyclopropyl-2,6,6-trimethylcyclohex-3-enyl ketone and the second material selected from the group consisting of δ-damascone, β-damascone, α-damascone and mixtures of δ-damascone, β-damascone, α-damascone is from 1.5:1 to about 10:1.

10. The fragrance mixture of claim 8 wherein the weight ratio of the first material cyclopropyl-2,6,6-trimethylcyclohex-3-enyl ketone and the second material: selected from the group consisting of δ-damascone, β-damascone, α-damascone and mixtures of δ-damascone, β-damascone, α-damascone is from 2:1 to about 8:1.

11. The fragrance mixture of claim 8 wherein the weight ratio of the first material cyclopropyl-2,6,6-trimethylcyclohex-3-enyl ketone and second material selected from the group consisting of δ-damascone, β-damascone, α-damascone and mixtures of δ-damascone, β-damascone, α-damascone is from about 3:1 to about 5:1.

12. A method for making, cyclopropyl-2,6,6-trimethylcyclohex-3-enyl ketone comprising the reaction of 4-acetyl-3,5,5-trimethylcyclohexene, ($C_1$–$C_6$)alkyl chloride magnesium and bromochloroethane.

13. The method of claim 12 wherein the ($C_1$–$C_6$)alkyl chloride magnesium is butyl magnesium chloride.

* * * * *